(12) United States Patent
Koseoglu et al.

(10) Patent No.: US 12,161,987 B2
(45) Date of Patent: Dec. 10, 2024

(54) HYDRODEARYLATION REACTOR

(71) Applicant: Saudi Arabian Oil Company, Dhahran (SA)

(72) Inventors: Omer Refa Koseoglu, Dhahran (SA); Robert Peter Hodgkins, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 607 days.

(21) Appl. No.: 17/404,853

(22) Filed: Aug. 17, 2021

(65) Prior Publication Data

US 2021/0370257 A1 Dec. 2, 2021

Related U.S. Application Data

(62) Division of application No. 16/597,752, filed on Oct. 9, 2019, now Pat. No. 11,110,428.

(51) Int. Cl.
| | |
|---|---|
| *C07C 4/12* | (2006.01) |
| *B01J 19/00* | (2006.01) |
| *B01J 19/24* | (2006.01) |
| *C07C 4/14* | (2006.01) |
| *C07C 4/16* | (2006.01) |
| *C07C 4/24* | (2006.01) |
| *C07C 37/52* | (2006.01) |
| *C10G 9/20* | (2006.01) |
| *C10G 69/06* | (2006.01) |

(52) U.S. Cl.
CPC ........... *B01J 19/243* (2013.01); *B01J 19/008* (2013.01); *B01J 19/242* (2013.01); *B01J 19/2435* (2013.01); *C07C 4/12* (2013.01); *C07C 4/14* (2013.01); *C07C 4/16* (2013.01); *C07C 4/24* (2013.01); *C07C 37/52* (2013.01); *C10G 9/20* (2013.01); *C10G 69/06* (2013.01); *B01J 2219/00083* (2013.01); *B01J 2219/00182* (2013.01)

(58) Field of Classification Search
CPC .... C07C 4/12; C07C 4/14; C07C 4/16; C07C 4/24; B01J 19/2415; B01J 19/242; B01J 18/242
See application file for complete search history.

(56) References Cited

U.S. PATENT DOCUMENTS

| | | |
|---|---|---|
| 2,885,452 A | 5/1959 | Louis |
| 3,062,903 A | 11/1962 | Odioso et al. |
| 3,084,022 A | 4/1963 | Sindery |

(Continued)

FOREIGN PATENT DOCUMENTS

| | | |
|---|---|---|
| CN | 107875977 | 4/2018 |
| EP | 0240340 | 10/1987 |

(Continued)

OTHER PUBLICATIONS

Electronic Supplementary Material for Chem Comm., The Royal Society of Chemistry, 2018, 189 pages.

(Continued)

*Primary Examiner* — Caixia Lu
(74) *Attorney, Agent, or Firm* — Fish & Richardson P.C.

(57) ABSTRACT

A system and method including providing a feed having alkyl-bridged multi-aromatic compounds to a tubular reactor, heating the tubular reactor, and cleaving an alkyl bridge of the alkyl-bridged multi-aromatic compounds.

11 Claims, 7 Drawing Sheets

(56) References Cited

U.S. PATENT DOCUMENTS

| | | | |
|---|---|---|---|
| 3,147,206 | A | 9/1964 | Tulleners |
| 3,390,200 | A | 6/1968 | Sze |
| 3,433,848 | A | 3/1969 | Devins |
| 3,441,625 | A | 4/1969 | Bargeron et al. |
| 3,518,182 | A | 6/1970 | Paterson |
| 3,531,537 | A | 9/1970 | Smith et al. |
| 3,641,190 | A | 2/1972 | Kilven et al. |
| 4,754,081 | A | 6/1988 | Mott |
| 4,837,403 | A | 6/1989 | Aumueller et al. |
| 4,869,833 | A | 9/1989 | Binning et al. |
| 5,409,675 | A | 4/1995 | Narayanan |
| 5,972,118 | A | 10/1999 | Hester et al. |
| 6,063,204 | A | 5/2000 | Hester et al. |
| 8,247,623 | B2 | 8/2012 | Vladea |
| 9,630,163 | B2 | 4/2017 | Rubio Martinez et al. |
| 10,053,401 | B1 * | 8/2018 | Beadle ................. C07C 4/24 |
| 10,294,172 | B2 | 5/2019 | Beadle et al. |
| 10,899,685 | B1 | 1/2021 | Koseoglu et al. |
| 2014/0110307 | A1 | 4/2014 | Salazar-Guillen et al. |
| 2018/0230070 | A1 | 8/2018 | Beadle et al. |
| 2019/0241486 | A1 | 8/2019 | Koseoglu et al. |
| 2021/0106971 | A1 | 4/2021 | Koseoglu et al. |

FOREIGN PATENT DOCUMENTS

| | | |
|---|---|---|
| EP | 1829920 | 9/2007 |
| WO | WO 2010101560 | 9/2010 |

OTHER PUBLICATIONS

GPCA, "R&I in the Digital Age," 6th edition, GPCA Research and Innovation Summit, Mar. 2019, 26 pages.

PCT International Search Report in International Appln. No. PCT/US2020/054822, dated Jan. 25, 2021, 16 page.

* cited by examiner

HYDRODEARYLATION REACTOR

CROSS-REFERENCE TO RELATED APPLICATION

This application is a divisional of and claims the benefit of priority to U.S. patent application Ser. No. 16/597,752, filed on Oct. 9, 2019, the contents of which are hereby incorporated by reference.

TECHNICAL FIELD

This disclosure relates to a hydrodearylation reactor that can perform hydrodearylation and hydrodealkylation in absence of catalyst.

BACKGROUND

Heavy crude oils usually contain more aromatics than do light crudes. Aromatic hydrocarbons are found in petroleum mixtures in the processing of crude oil. Under standard conditions, lower aromatics such as benzene, toluene, and xylene are in liquid form. In contrast, some higher aromatics may occur as solids in isolation but dissolve to form a liquid solution with simple aromatics. Aromatics found in crude oil and petroleum products include mono-aromatic compounds such as benzene derivatives having methyl, ethyl, propyl, or higher alkyl groups attached to the benzene ring. This series of aromatics may be called alkylbenzenes having the general formula of $C_nH_{2n-6}$ (where n≥6). An aromatic series with only one benzene ring may be called mono-aromatics, mononuclear aromatics, or monocyclic aromatics. Heavy fractions commonly have aromatic compounds with multiple benzene rings. Heavy petroleum fractions and residues contain heavy aromatic compounds each having more than one benzene ring. Again, such heavy aromatics may exist as solids in isolation. These multi-aromatic hydrocarbons (e.g., found in heavier fractions than naphtha) in combination with heterocyclic compounds may be major constituents of heavy crudes and crude residues.

Lower members of aromatic compounds are present in small amounts in crude oils and light petroleum fractions. The simplest mononuclear aromatic compound is benzene (C6H6). Toluene (C7H8) and xylene (C8H10) are also mononuclear aromatic compounds found in variable amounts in crude oils. Benzene, toluene, and xylenes (BTX) are petrochemical intermediates and gasoline components. Separating BTX aromatics from crude oil distillates is generally not feasible because BTX aromatics are present in low concentrations. Enriching a naphtha fraction with BTX aromatics is possible through a catalytic reforming process. As indicated, in the petroleum refining and petrochemical industries, BTX refers to mixtures of benzene, toluene, and the three xylene isomers, all of which are aromatic hydrocarbons. If ethylbenzene is included, the mixture is sometimes referred to as BTEX. Benzene, toluene, and xylenes can be made by various processes.

BTX production may be based on the recovery of aromatics derived from the catalytic reforming of naphtha in a petroleum refinery or aromatics complex. Catalytic reforming typically utilizes a feedstock naphtha that contains non-aromatic hydrocarbons with 6 to 11 or 12 carbon atoms and produces a reformate product containing C6 to C8 aromatics (benzene, toluene, xylenes) as well as paraffins and heavier aromatics containing 9 to 11 or 12 carbon atoms. Another process for producing BTX aromatics involves the steam cracking of hydrocarbons which generally produces a cracked naphtha product commonly referred to as pyrolysis gasoline, pyrolysis gas, or pygas. The pyrolysis gasoline generally consists of C6 to C8 aromatics, heavier aromatics including C9 to C11 or C12 aromatics, and non-aromatic cyclic hydrocarbons containing 6 or more carbon atoms. A majority of the global production of benzene is by extraction from either reformate or pyrolysis gasoline. The BTX aromatics can be extracted from catalytic reformate or from pyrolysis gasoline by many different techniques.

SUMMARY

An aspect relates to a method of processing alkyl-bridged multi-aromatic compounds. The method includes providing a feed including an alkyl-bridged multi-aromatic compound to a coiled tubular reactor. The alkyl-bridged multi-aromatic compound includes a first aromatic ring coupled via an alkyl bridge to a second aromatic ring. The alkyl bridge has at least two carbons. The method includes heating the coiled tubular reactor and cleaving the alkyl bridge in the coiled tubular reactor to separate the alkyl-bridged multi-aromatic compound into a first aromatic compound having the first aromatic ring and a second aromatic compound having the second aromatic ring Another aspect relates to method of processing alkyl-bridged multi-aromatic compounds. The method includes feeding alkyl-bridged multi-aromatic compounds each having an alkyl bridge to a coiled tubular reactor, wherein the coiled tubular reactor does not include catalyst. The method includes feeding hydrogen to the coiled tubular reactor and providing heat from a furnace to heat the coiled tubular reactor, wherein at least a portion of the coiled tubular reactor is disposed in the furnace. The method includes performing hydrodearylation on the alkyl-bridged multi-aromatic compounds in the coiled tubular reactor via the hydrogen and via the heat provided by the furnace. The hydrodearylation involves breaking a carbon-carbon bond of the alkyl bridge of at least some of the alkyl-bridged multi-aromatic compounds.

Yet another aspect relates to a method of operating a hydrodearylation reactor. The method includes preheating a hydrocarbon feed having alkyl-bridged multi-aromatic compounds. The method includes flowing the hydrocarbon feed and hydrogen through a coiled tubular reactor and heating the coiled tubular reactor with a furnace, wherein at least a portion of the coiled tubular reactor is disposed in the furnace. The method includes breaking a carbon-carbon bond of an alkyl bridge in the coiled tubular reactor in absence of catalyst. The method includes discharging an effluent from the coiled tubular reactor.

Yet another aspect relates to a hydrocarbon processing system including a hydrodearylation reactor system that receives hydrocarbon feed and hydrogen. The hydrocarbon feed includes an alkyl-bridged multi-aromatic compound having a first aromatic ring coupled via an alkyl bridge to a second aromatic ring. The hydrodearylation reactor system includes a hydrodearylation reactor that is a coiled tubular reactor to break a carbon-carbon bond of the alkyl bridge in presence of hydrogen to separate the first aromatic ring from the second aromatic ring, wherein the coiled tubular reactor does not include catalyst. The hydrodearylation reactor system includes a furnace to heat the coiled tubular reactor, wherein at least a portion of the coiled tubular reactor is disposed in the furnace. The hydrocarbon processing system includes a separation system that receives an effluent including unreacted hydrogen from the coiled tubular reactor. The separation system has a cold separator vessel to discharge overhead light components including unreacted hydrogen and to discharge bottoms liquid.

Yet another aspect relates to an aromatics processing system including an aromatics complex having a xylene distillation column that discharges an overhead stream including mixed xylenes and discharges a bottoms stream including C9+ aromatic compounds. The aromatics processing system includes a coiled tubular reactor that receives feed having at least a portion of the bottoms stream including alkyl-bridged multi-aromatic compounds. The coiled tubular reactor breaks a carbon-carbon bond of an alkyl bridge of an alkyl-bridged multi-aromatic compound and discharges a product effluent. The aromatics processing system includes (1) a conduit to add hydrogen to the feed upstream of the coiled tubular reactor or directly to the coiled tubular reactor, (2) a furnace that provides heat to the coiled tubular reactor (wherein at least a portion of the coiled tubular reactor is disposed in the furnace), and (3) a heat exchanger that heats the feed with the product effluent.

Yet another aspect relates to a hydrodearylation reactor system including a feed conduit operationally coupled to an aromatics complex to receive a hydrocarbon feed including alkyl-bridged multi-aromatic compounds. The aromatics complex includes a distillation column. The hydrodearylation reactor system has a coiled tubular reactor operationally coupled to the feed conduit that receives the hydrocarbon feed and cleaves an alkyl bridge of an alkyl-bridge multi-aromatic compound of the received alkyl-bridge multi-aromatic compounds in presence of hydrogen. The hydrodearylation reactor system includes (1) a hydrogen conduit to add hydrogen to the feed conduit or directly to the coiled tubular reactor, (2) a furnace that heats the coiled tubular reactor, (3) a discharge conduit to discharge an effluent from the coiled tubular reactor, and (4) a heat exchanger that heats the hydrocarbon feed with the effluent.

The details of one or more implementations are set forth in the accompanying drawings and the description below. Other features and advantages will be apparent from the description and drawings, and from the claims.

DETAILED DESCRIPTION

Some aspects of the present disclosure are directed to providing a feed having alkyl-bridged multi-aromatic compounds to a coiled tubular reactor and heating the reactor to cleave alkyl bridges in presence of hydrogen but in absence of catalyst. An alkyl-bridged multi-aromatic compound may have a first aromatic ring coupled via an alkyl bridge to a second aromatic ring. The cleaving of the alkyl bridge in the coiled tubular reactor may separate the alkyl-bridged multi-aromatic compound into a first aromatic compound having the first aromatic ring and a second aromatic compound having the second aromatic ring. The alkyl bridge may have at least two carbons. The cleaving may break a carbon-carbon bond of the alkyl bridge. The cleaving of the alkyl bridge may be labeled as hydrodearylation.

Hydrodearylation reactions in the presence of a catalyst typically require temperatures between 250° C. to 450° C. In contrast, without catalyst, temperature may be increased to at least 500° C. to induce thermal cracking to perform the hydrodearylation. Hydrodearylation may be implemented, for example, at temperatures in a range of 500° C. to 750° C. and with relatively short residence time (e.g., less than 50 seconds) to avoid or reduce coke formation in the reactor. The degree of hydrodearylation (and hydrodealkylation) generally increases as the temperature increases through this temperature range. The reactor can be designed to carry-out both hydrodearylation and hydrodealkylation reactions. This reactor may carry-out both hydrodearylation and hydrodealkylation reactions, for example, on a bottoms reject stream from an aromatic complex. Hydrodealkylation may be a chemical reaction involving reacting an aromatic hydrocarbon in the presence of hydrogen to form a simpler aromatic hydrocarbon having less functional groups. An example is conversion of toluene to benzene. Another example is the conversion of 1,2,4-trimethylbenzene to xylene.

Embodiments of the present techniques may include a coiled-tubular reactor operating at a residence time less than 100 seconds in performing hydrodearylation and hydrodealkylation reactions. In implementations, the reactor may facilitate BTX make from a low-value aromatics reject stream in the absence of a catalyst. The reactor may carry-out reactions, such as hydrodearylation reactions, that rely on temperatures greater than 450° C. and can benefit from short residence times (e.g., less than 30 seconds). The tubular reactor may be coiled to have a shorter reactor length (footprint) from inlet to outlet of the reactor. The reactor may made of a tube coiled in a circular spiral shape to increase the flow length of the tube with less corresponding increase in longitudinal length. The reactor includes an inlet to receive feedstock and outlet to discharge products. In operation, the fluid flow through the reactor may be generally plug flow in certain instances.

Figure 1:
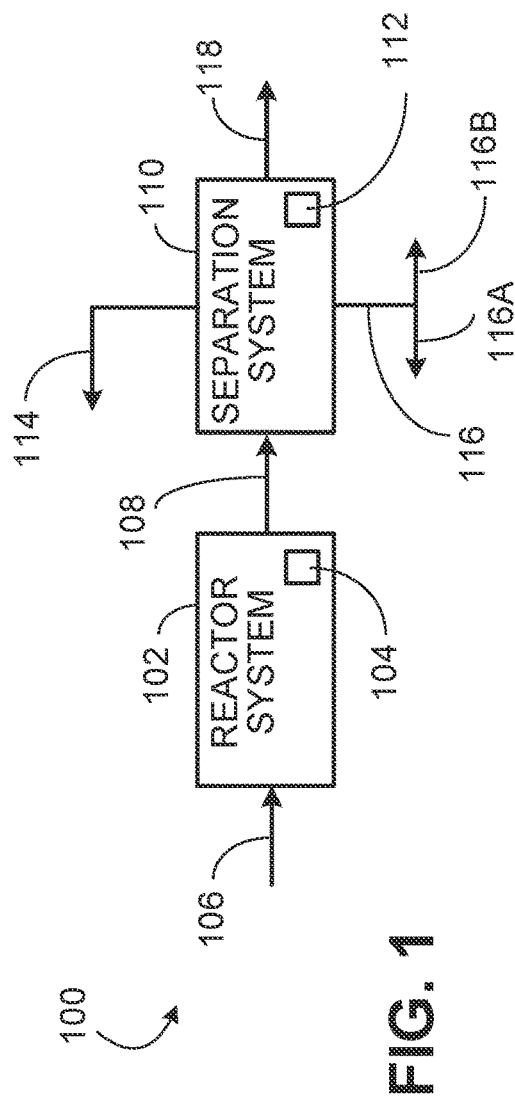
FIG. 1 is a block diagram of a hydrocarbon processing system including a reactor system (e.g., hydrodearylation reactor system) having a reactor (e.g., hydrodearylation reactor).

FIG. 1 is a hydrocarbon processing system 100 including a reactor system 102 (e.g., hydrodearylation reactor system) having a reactor 104 (e.g., hydrodearylation reactor). The reactor 104 may be a tubular reactor that is a hydrodearylation reactor, as discussed below. The tubular reactor may be a coiled tubular reactor. Embodiments of the reactor 104 do not include catalyst. The reactor 104 can perform the hydrodearylation in the absence of catalyst. The reactor 104 can produce benzene, toluene, and mixed xylenes (BTX) from heavy aromatic compounds. More than one reactor 104 may be employed. Multiple reactors 104 (e.g., coiled tubular reactors) may be operationally disposed in parallel or series, or some combination thereof.

In operation, the hydrocarbon processing system 100 receives a hydrocarbon feed 106 that may be processed by the reactor 104. The hydrocarbon feed 106 includes heavy aromatic compounds, such as C9+ aromatic compounds (alkyl aromatic compounds). The C9+ aromatic compounds can include di, tri, and poly aromatics (C9 to C16+).

The C9+ aromatic compounds may include mono-aromatic compounds having a single aromatic (benzene) ring. The C9+ aromatic compounds include multi-aromatic compounds having at least two aromatic (benzene) rings. The at least two benzene rings may each be an alkyl aromatic ring in having at least one alkyl group bonded to a carbon of the benzene ring.

These multi-aromatic compounds as heavy aromatic compounds in the hydrocarbon feed 106 include alkyl-bridged multi-aromatic compounds. The alkyl-bridged multi-aromatic compounds include at least two benzene rings connected by an alkyl bridge group having at least two carbons. The benzene rings are connected to different carbons of the alkyl bridge group. The benzene rings individually may each be an alkyl benzene ring in having an alkyl group (bonded to a carbon of the benzene ring) not associated with the alkyl bridge group. The alkyl-bridged multi-aromatic compounds may be non-condensed multi-aromatic compounds in not having condensed benzene rings. The alkyl-bridged multi-aromatic compounds may include alkyl-bridged non-condensed alkyl aromatic compounds. Examples of the alkyl-bridged multi-aromatic compounds include Formula I, Formula II, and Formula III:

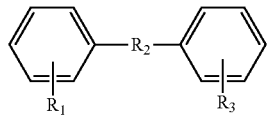

[Formula I]

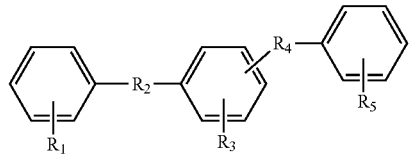

[Formula II]

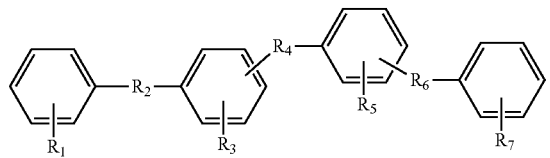

[Formula III]

R2, R4, and R6 are alkyl bridge groups independently having from two to six carbon atoms. R1, R3, R5, and R7 are independently selected from the group consisting of hydrogen and an alkyl group having from one to eight carbon atoms. In addition to the groups R1, R3, R5, and R7, the benzene groups of Formulas I, II, and III may further include additional alkyl groups connected to the benzene groups, respectively. In addition to the four benzene groups of Formula III, the alkyl-bridged multi-aromatic compounds may include five or more benzene groups connected by alkyl bridges, where the additional benzene groups further may include alkyl groups connected to the additional benzene groups.

The reactor 104 may receive the hydrocarbon feed 106. The reactor system 102 includes a conduit to add hydrogen to the feed 106 conduit or directly to the reactor 104. In operation, the reactor 104 cleaves the alkyl bridge (e.g., R2, R4, or R6 depicted above) between aromatic compounds (of the alkyl-bridged multi-aromatic compounds) in the presence of the hydrogen. The cleaving of the alkyl bridge may be to break a carbon-carbon bond of the alkyl bridge. Hydrodearylation may be defined herein as the cleaving of an alkyl bridge between aromatic compounds of an alkyl-bridged multi-aromatic compound. The hydrodearylation of the alkyl-bridged multi-aromatic compounds may give mono-aromatic compounds (e.g., benzene, toluene, mixed xylenes, and heavier alkyl mono-aromatic compounds) and simpler multi-aromatic compounds.

These compounds generated by the hydrodearylation may be made lighter by hydrodealkylation in the reactor 104. In other words, the hydrodealkylation may further simplify alkyl mono-aromatic compounds and remaining multi-aromatic compounds by replacing one or more carbons in attached alkyl groups with hydrogen. Such hydrodealkylation of the alkyl mono-aromatic compounds may increase production of benzene and also toluene or mixed xylenes in certain implementations. The impact of the hydrodealkylation may depend, for example, on the composition of the feed 106 and on the operating conditions of the reactor 104.

The reactor 104 may perform this hydrodealkylation (in the presence of hydrogen) on the aromatic compounds of the alkyl-bridged multi-aromatic compounds before, during, or after the cleaving of the alkyl bridge. The reactor 104 may perform hydrodealkylation (in the presence of the hydrogen) of alkyl mono-aromatic compounds that enter in the hydrocarbon feed 106. Again, the hydrodealkylation of alkyl mono-aromatic compounds (generated from the hydrodearylation or entering in the feed 106) may give benzene and also toluene and mixed xylenes in some instances.

In the hydrodearylation (with or without hydrodealkylation) in the reactor 104, the reactor system 102 converts heavy aromatic compounds entering in the feed 106 into relatively lighter aromatic compounds. Therefore, the reactor system 102 discharges processed hydrocarbons 108 (e.g., a product effluent of the reactor 104) that may include a mass per time rate of more mono-aromatic compounds and less multi-aromatic compounds than in the feed 106. The processed hydrocarbons 108 stream may include a greater mass per time rate of lighter alkyl aromatic compounds and benzene than in the hydrocarbon feed 106. In implementations, the processed hydrocarbons 108 stream may include a mass per time rate of BTX greater than in the hydrocarbon feed 106. The average molecular weight of compounds in the processed hydrocarbons 108 may be less than the average molecular weight of compounds in the hydrocarbon feed 106.

As one example with the R2 bridge (Formula I) above as —C2H4-(having two carbons), the hydrodearylation may cleave the bond between the two carbons separating the two depicted aromatic rings with each having an attached —CH3 group from the cleaved R2 alkyl bridge in presence of hydrogen. Hydrodealkylation may then replace the —CH3 group with hydrogen (H) in some instances. In certain embodiments, hydrodealkylation may also replace R1 and R3 in Formula I with hydrogen (H) if R1 and R3 are not hydrogen (H). Formula II and Formula III (or comparable structures) may experience similar scenarios when subjected to hydrodearylation and hydrodealkylation.

Formula IV below is an example of a mono-aromatic compound that might be separated (formed) from an alkyl-bridged multi-aromatic compound via hydrodearylation. R1 below is independently selected from the group consisting of hydrogen and an alkyl group having from one to eight carbon atoms, R2 below is independently selected from the group consisting of hydrogen and an alkyl group having from one to eight carbon atoms. In some implementations, the selectivity of benzene formation (i.e., with R1 and R2 each as hydrogen) from the hydrodearylation may be lower the selectivity of toluene and xylenes.

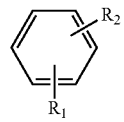

[Formula IV]

The hydrocarbon processing system 100 includes a separation system 110 having at least one vessel 112 for further processing of the processed hydrocarbons 108. In the illustrated embodiment, the reactor system 102 discharges the processed hydrocarbons 108 as feed to the separation system 110. The separation system 110 may remove light components 114 (e.g., including unreacted hydrogen) from the processed hydrocarbons 108 for recycle to the reactor system 102 or sent to other users. In implementations, the light components 114 include at least 60 weight percent (wt %) of hydrogen. The hydrogen in the light components 114 may primarily be unreacted hydrogen that was fed to the reactor 104. In some cases, the hydrogen in the light components 114 may also include any hydrogen generated in the hydrodearylation (and hydrodealkylation) in the reactor 104.

The separation system 110 may remove heavy components 116 from the processed hydrocarbons 108 for recycle 116A to the reactor system 102 to be included, for example, with the hydrocarbon feed 106. The heavy components 116 may include alkyl-bridged multi-aromatic compounds. The alkyl-bridged multi-aromatic compounds may include unreacted alkyl-bridged multi-aromatic compounds from the hydrocarbon feed 106 and that discharged in the processed hydrocarbons 108. The alkyl-bridged multi-aromatic compounds may include alkyl-bridged multi-aromatic compounds from the hydrocarbon feed 106 that were simplified in the reactor system 102 and discharged as simplified alkyl-bridged multi-aromatic compounds in the processed hydrocarbons 108. A portion 116B of the heavy components 116 may be removed (e.g., bled) from the hydrocarbon processing system 100 to prevent accumulation of heavy components in the system 100.

The separation system 110 may discharge at least one product stream 118 including components from the processed hydrocarbons 108 not removed as light components 114 and heavy components 116. In some implementations, the one or more product streams may be sent, for example, to an aromatics complex for further processing.

The hydrocarbon processing system 100 (including both the reactor system 102 and separation system 110) may generally be a continuous operation. The reactor 104 (e.g., coiled tubular reactor) may be a continuous reactor that processes the hydrocarbon feed 106 and discharges processed hydrocarbons 108 as effluent. The separation system 110 may operate in tandem with the reactor system 102 to further process the processed hydrocarbons 108 and discharge product streams 118 and optionally recycle streams.

In certain embodiments, the at least one vessel 112 in the separation system 110 includes a first separation vessel and a second separation vessel disposed in series. The first separation vessel and the second separation vessel may each be, for example, a vertical vessel having a volume and length to diameter (L/D) ratio, as well as internals in some implementations, to provide for separation of gas and liquid. In implementations, these separation vessels may be labeled, for example, as a separator or knockout drum, and the like.

The processed hydrocarbons 108 may be fed to the first separation vessel to provide a first light stream and a first heavy stream from the first separation vessel. The first light stream may be fed to the second separation vessel to provide a second light stream and a second heavy stream. The second light stream (from the second separation vessel) may be the light components 114 stream discharged from the separation system 110. In some embodiments, the light components 114 may be a recycled hydrogen stream or processed to provide a recycled hydrogen stream. In particular embodiments, the recycled hydrogen may be combined with a makeup hydrogen stream to provide the hydrogen supplied to the reactor system 102 and the reactor 104.

In some implementations, the first heavy stream (from the first separation vessel) and the second heavy stream (and the second separation vessel) may be combined to give a combined heavy stream that is subjected to further processing (separations) to give the one or more product streams 118. For example, the at least one vessel 112 may further include a first distillation column (a first fractionator) and a second distillation column (a second fractionator).

The combined heavy stream may be fed to the first distillation column for fractionating into a first light fractionation stream (e.g., as a first product stream 118) and a first heavy fractionation stream. The first heavy fractionation stream may be fed to the second distillation column for fractionating into a second light fractionation stream (e.g., as a second product stream 118) and a second heavy fractionation stream. At least portions of the first light fractionation stream and the second light fractionation stream may be fed to an aromatics complex to recover BTX.

In various embodiments, the second heavy fractionation stream (from the second distillation column) may be the heavy components 116 discharged from the separation system 110. A portion (e.g., recycle 116A) of the second heavy fractionation stream may be recycled to the reactor 104. In some examples, a portion (e.g., heavy components 116B) of the second heavy fractionation stream may be a bleed stream to prevent buildup of alkyl aromatic compounds (e.g., non-condensed) including alkyl-bridged multi-aromatic compounds in various process flow streams in the hydrocarbon processing system 100. A flow rate of the bleed stream may be adjusted accordingly to facilitate prevention of undesired buildup of heavy aromatic hydrocarbon in the hydrocarbon processing system 100. Other configurations of the separation system 110 are applicable.

Figure 2:
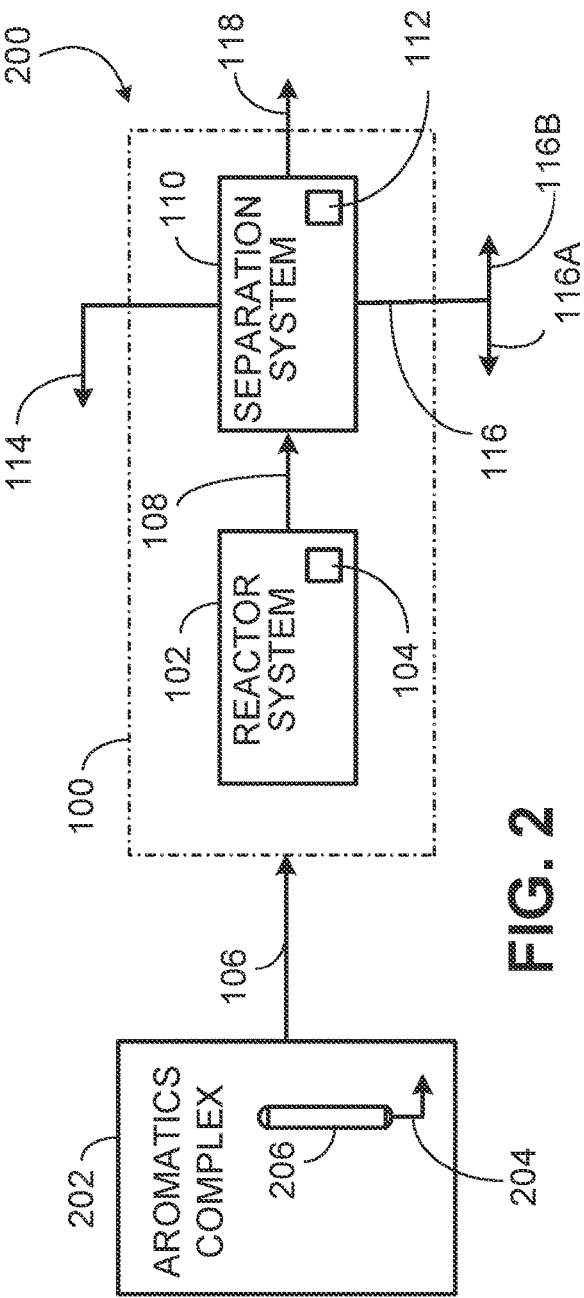
FIG. 2 is a block diagram of an aromatics processing system that includes the hydrocarbon processing system of FIG. 1 operationally coupled to an upstream aromatics complex.

FIG. 2 is an aromatics processing system 200 that includes the hydrocarbon processing system 100 of FIG. 1 operationally coupled to an upstream aromatics complex 202 (aromatics recovery complex). The aromatics complex 202 may convert, for example, naphtha or pyrolysis gasoline into BTX. As previously indicated, the acronym "BTX" is for "benzene, toluene, and mixed xylenes."

In the illustrated embodiment, the aromatics complex 202 provides at least a portion of the hydrocarbon feed 106 to the reactor system 102. A storage vessel or feed tank, or both, for the provided hydrocarbon feed 106 may be operationally disposed between the aromatics complex 202 and the hydrocarbon processing system 100.

The aromatics complex 202 may separate a mixture of aromatic compounds into respective product streams of benzene, toluene, and mixed xylenes products. There are many configurations of an aromatics complex 202. In one implementation, the aromatics complex 202 may include, for example, a dehexanizer distillation column that removes lighter components and discharges a bottoms product stream. The bottoms product stream may be fed to a benzene distillation column that removes benzene overhead and discharges a bottoms stream having, for example, toluene, mixed xylenes, ethyl benzene, and C9+ aromatic compounds. In some instances, the overhead discharge may enter absorber and stripper columns to purify the benzene. The bottoms stream from the benzene distillation column may be processed in absorber and stripper columns (e.g., to remove light components) and further in distillation columns. The aforementioned absorber and stripper columns may involve solvent extraction.

This bottoms stream from the benzene distillation column may ultimately be processed in distillation columns to separate and recover toluene and various mixed xylenes. The distillation columns may include a toluene distillation column(s) and a xylene distillation column(s). A toluene distillation column may separate and discharge toluene overhead. The xylene distillation column may receive the bottoms discharge from the toluene distillation column, separate and discharge mixed xylenes overhead and discharge a heavy aromatics (C9+) bottoms stream. The mixed xylenes discharged overhead from the xylene distillation column may be further separated or processed, for example, into streams of para-xylene, meta-xylene, ortho-xylene, ethyl benzene, and C9+ aromatic compounds, respectively. In some cases, additional processing may be implemented, for example, to increase production of benzene and para-xylene. Moreover, in certain instances, a heavy aromatics column may process C9+ aromatic compounds. Further, an aromatics complex may have different conversion processes that generate heavier aromatics such as C16+ aromatic compounds. The C9+ aromatics (and C16+ aromatics) may include alkyl-bridged multi-aromatic compounds.

In all, certain bottoms streams (e.g., a discharge from a bottom portion of a distillation column) in the aromatics complex 202 include C9+ aromatic compounds that may include C16+ aromatic compounds. These bottoms streams rich in heavy aromatic compounds may be known as a heavy-aromatics bottoms stream, an aromatics bottoms stream, a reject stream, or a C9+ reject stream, and the like, in or from an aromatics complex 202. An example of a heavy-aromatics bottoms stream(s) 204 may be from a xylene distillation column(s) 206.

In the illustrated embodiment, the aromatics complex 202 includes at least one xylene distillation column 206 that discharges a heavy-aromatics bottoms stream 204 having C9+ aromatic compounds and which may include C16+ aromatic compounds. The heavy-aromatics bottoms stream 204 includes alkyl-bridged multi-aromatic compounds that may include non-condensed alkyl-bridged multi-aromatic compounds.

The xylene distillation column 206 may be a xylene distillation column that discharges mixed xylenes overhead. The xylene distillation column 206 may be a xylene rerun distillation column that discharges mixed xylenes overhead. In some implementations, the xylene distillation column 206 may additionally receive feed having heavy aromatic compounds from other equipment, such as a transalkylation unit.

The aromatics complex 202 may discharge the heavy-aromatics bottoms stream 204 as the hydrocarbon feed 106 to the hydrocarbon processing system 100. In some implementations, the aromatics complex 202 may remove C9 and C10 components from the heavy-aromatics bottoms stream 204 before providing the stream 204 as the feed 106 to the hydrocarbon processing system 100. The aromatics complex 202 may process the heavy-aromatics bottoms stream 204, such as in a heavy aromatics distillation column, and thus send a processed heavy-aromatics bottoms stream as the hydrocarbon feed 106 to the hydrocarbon processing system 100. The aromatics complex 202 may have additional sources of C9+ (and C11+ or C16+) aromatic compounds (including alkyl-bridged multi-aromatic compounds) other than the heavy-aromatics bottoms streams 204 for supply as hydrocarbon feed 106 to the hydrocarbon processing system 100.

Features of the hydrocarbon processing system 100 depicted in FIG. 2 have been described above with respect to FIG. 1. However, it should be noted that the product stream(s) 118 from the hydrocarbon processing system 100 may be sent to the aromatics complex 202 in certain embodiments, such as for the further recovery of BTX in the product streams 118.

In embodiments, the hydrocarbon feed 106 may be or include a heavy hydrocarbons stream. In some implementations, the heavy hydrocarbons stream may be C9+ or C10+ from a xylene rerun column or a heavy aromatic column bottoms from a para-xylene unit in an aromatics complex. In certain embodiments, the feed 106 may include C9 to C16+ aromatic compounds and may be predominantly mono-aromatics, di-aromatics, and poly-aromatics.

Figure 3:
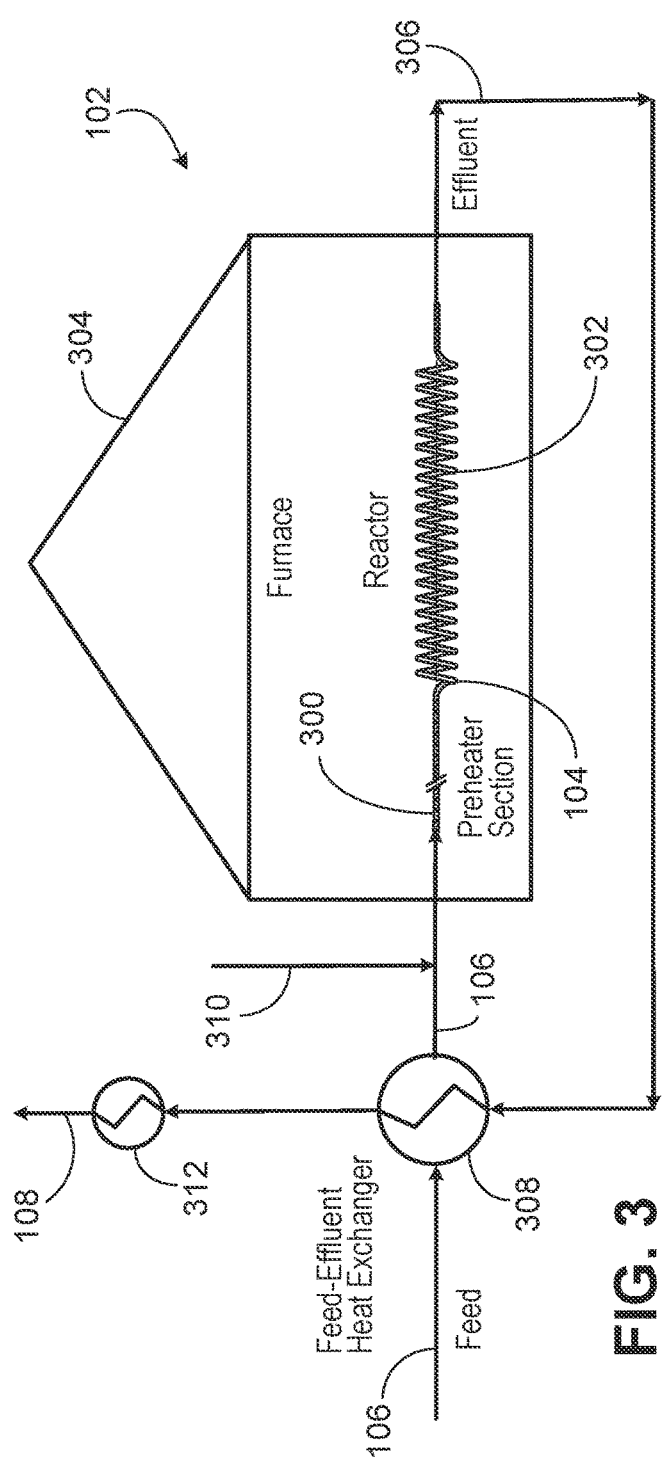
FIG. 3 is a diagram of an embodiment of the reactor system depicted in FIGS. 1-2.

FIG. 3 is an embodiment of a reactor system 102 depicted in FIGS. 1-2. In this embodiment, the reactor 104 of the reactor system 102 is a coiled tubular reactor. The reactor 104 has a straight-run section 300 at an inlet portion of the reactor 104 and a coiled tubular section 302. In the depicted embodiment, the reactor 104 does not include catalyst. The coiled configuration may provide the benefit of a shorter footprint of the reactor as compared to a tubular reactor not having a coiled configuration. The reactor 104 internal diameter and length may be designed for typical operating conditions to have a total residence time between 0.3 second and 1000 seconds, between 0.5 second and 100 seconds, or between 1 second and 30 seconds.

In the illustrated embodiment, the reactor 104 is disposed in a furnace 304 that heats the reactor 104. In operation, the furnace 304 transfers heat to the fluid in the reactor 104. In certain implementations, the straight-run section 300 may be a preheating section in which the furnace heats the hydrocarbon feed 106 to a desired temperature prior to the feed 106 entering the coiled tubular section 302.

A furnace is a device used for high-temperature heating. The heat energy to fuel a furnace may be supplied directly by fuel combustion, by electricity such as the electric arc furnace, or through induction heating in induction furnaces. The furnace can be a direct fired heater, a cracking furnace, a thermal cracking furnace, a pyrolysis furnace, and so on. The furnace as a direct fired heater may have a burner to provide hot gasses that transfer their heat energy to process fluid (feed 106, reaction mixture, etc.) flowing through the piping (e.g., straight piping, piping coils, etc.) of the reactor 104.

The hydrocarbon feed 106 may be fed to the reactor 104 in liquid phase or gas phase, or both. The hydrocarbon feed 106 (e.g., liquid phase) and hydrogen (gas phase) streams may be added to the reactor at the same time and location. Alternatively, the hydrocarbon feed 106 (liquid phase) and hydrogen (gas phase) may be added sequentially at different locations. Alternatively, both liquid and gas phase streams are added sequentially at multiple locations.

In certain embodiments, steam may be added as a co-stream to the reactor 104 to reduce coke formation in the reactor 104. The weight ratio of steam to hydrocarbon may be less than 0.1, less than 0.01, or less than 0.001. Alternatively, alkyl sulfide or disulfides, such as disulfide oil (e.g., dimethydisulfide), may added as an additive to the feed 106 to reduce coke formation or plugging in the reactor 104, and to also protect the interior surface of the metal coiled tubular reactor 104. The concentration of disulfide oil in the feed 106 may be less than 1000 parts per million (ppm), less than 100 ppm, or less than 10 ppm.

In operation, the reactor 104 receives the hydrocarbon feed 106 and performs hydrodearylation and hydrodealkylation, as discussed above with respect to FIG. 1. The operating conditions of the reactor may include, for example, an operating pressure of less than 150 bars, an operating temperature in a range of 500° C. to 750° C., or 550° C. to 700° C., a flow rate of the feed 106 or reaction mixture through the reactor 104 of less than 100,000 liters per hour (L/h) or less than 30,000 L/h, and a residence of less than 150 seconds or less than 50 seconds. In the illustrated embodiment, the reactor 104 in operation discharges an effluent 306 that may be compositionally the same as the processed hydrocarbons 108 discussed with respect to FIG. 1.

The reactor system 102 may optionally include a heat exchanger 308 to heat the hydrocarbon feed 106 with the effluent 306. In operation in the heat exchanger 308, heat transfer may occur from the effluent 306 to the hydrocarbon feed 106. Thus, the hydrocarbon feed 106 that discharges from the heat exchanger 308 is preheated hydrocarbon feed 106. The effluent 306 that discharges from the heat exchanger 308 is cooled effluent 306. The heat exchanger 308 may be, for example, a shell-and-tube heat exchanger. The effluent 306 may flow through the tube side and the hydrocarbon feed 106 flows through the shell side. On the other hand, the effluent 306 may flow through the shell side and the hydrocarbon feed 106 flows through the tube side. In some implementations in the heat exchanger 308, the flow of the effluent 306 may be countercurrent with the flow of the hydrocarbon feed 106.

The reactor system 102 includes a conduit to add hydrogen 310 to the hydrocarbon feed 106 for the hydrodearylation and hydrodealkylation in the reactor 104. The hydrogen 310 may be fresh hydrogen. The hydrogen 310 stream may be a combination of recycle hydrogen and fresh hydrogen as makeup. For example, the light components 114 (FIG. 1) giving recycle hydrogen may be combined with fresh hydrogen to give the hydrogen 310 stream.

Thus, the hydrogen 310 may include light components in addition to hydrogen. The hydrogen 310 may be added to a conduit conveying the hydrocarbon feed 106 to the reactor 104. While the hydrogen 310 is depicted as added to the feed 106 downstream of the heat exchanger 308, the hydrogen 310 may instead be added to the feed 106 upstream of the heat exchanger 308. Moreover, the hydrogen 310 may instead be added directly to the reactor 104 in the furnace 304.

In implementations, the fluid flow through the reactor 104 may be plug flow or approach plug flow. The flow of the feed 106 (and hydrogen) through the reactor 104 may be generally plug flow The flow of this reaction mixture through the reactor 104 may be 95% to 100% plug flow or may be, for example, 90% plug flow with 10% axial dispersion (mixing).

The reactor system 102 may optionally include a cooler 312 to cool the effluent 306 (or further cool the effluent 306 if the upstream feed-effluent cross-exchanger 308 is employed). The cooler 312 may be a heat exchanger, such as a shell-and-tube heat exchanger, plate heat exchanger, plate-and-frame heat exchanger, air-cooled heat exchanger (e.g., finned tube), or other type of heat exchanger. The cooling medium may be, for example, water, air, glycol, oil, and so forth.

The cooled effluent 306 may discharge from the cooler 312 as the processed hydrocarbons 108 stream (FIGS. 1-2). As mentioned, the processed hydrocarbons 108 stream may be the effluent 306. Moreover, absent the heat exchangers 308 and 312, the processed hydrocarbons 108 may have the same temperature as the effluent 306 at the reactor 104 discharge minus any ambient losses of heat.

Figure 4:
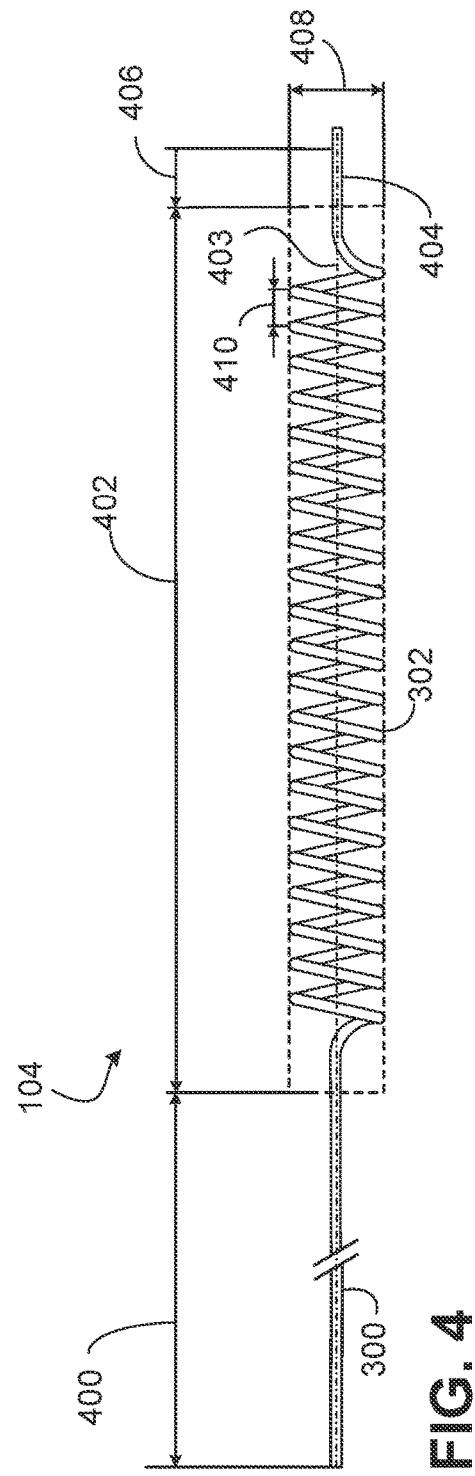
FIG. 4 is a perspective view of an implementation of a hydrodearylation reactor that is a coiled tubular reactor that may disposed (or partially disposed) in a furnace as a component of a reactor system of FIGS. 1-3.

FIG. 4 is an implementation of a hydrodearylation reactor 104 that is a coiled tubular reactor that may disposed (or partially disposed) in a furnace 304 (FIG. 3) as a component of the reactor system 102. The coiled tubular reactor 104 may have a straight-run section 300 of pipe and the coiled section 302 of the pipe. Incorporating a coiled section of pipe instead of having only straight pipe can beneficially provide for a shorter footprint of the reactor 104. While a coiled section 302 is depicted, other embodiments may include, for example, a stack tube arrangement of the pipe instead of coiled pipe. The reactor 104 may provide for desired residence time at a desired footprint of the reactor 104. The metallurgy of the pipe may be, for example, a stainless steel or a nickel alloy.

In implementations, the pipe forming the reactor 104 may have an inner diameter in a range of 40 millimeters (mm) to 200 mm (or 50 mm to 180 mm), or at least 150 mm. The longitudinal length of the reactor 104 may be, for example, in a range of 6000 mm to 10,000 mm. The length 400 of the straight-run section 300 may be, for example, in the range of 4000 mm to 8000 mm, or at least 5000 mm. The longitudinal length 402 of the coiled section 302 may be in the range of 2000 mm to 10,000 mm or in the range of 2000 mm to 6000 mm, or at least 3000 mm. The coils (spirals) are around a longitudinal axis 403 of the reactor 102. The reactor 102 may include a straight-run discharge portion 404 having a length 406 of at least 200 mm As for the coils in the coiled section 302, the number of coils (spirals) may be at least 20 or at least 25. The length of a spiral may be at least 2000 mm or at least 2500 mm. The volume of a spiral may be, for example, in a range of 15 cubic meters (m3) to 210 m3, at least 60 m3, or at least 150 m3. The circumference 408 of the coils (spirals) may be, for example, in a range of 500 mm to 4000 mm, or at least 1500 mm. The pitch 410 between coils (spirals) may be, for example, in the range of 70 mm to 700 mm, less than 600 mm, or less than 500 mm. These aforementioned numerical values and ranges for the various features and dimensions are exemplary and not meant to limit the present techniques.

In operation, the reactor 104 may provide a residence time of the feed and reaction mixture through the reactor in a range of 1 second to 500 seconds, 2 seconds to 300 seconds, 3 seconds to 200 seconds, 4 seconds to 100 seconds, 5 seconds to 50 seconds, 6 seconds to 40 seconds, and 7 seconds to 30 seconds. The residence time may be less than 500 seconds, less than 300 seconds, less than 200 seconds, less than 100 seconds, less than 50 seconds, less than 40 seconds, and less than 30 seconds.

Figure 5:
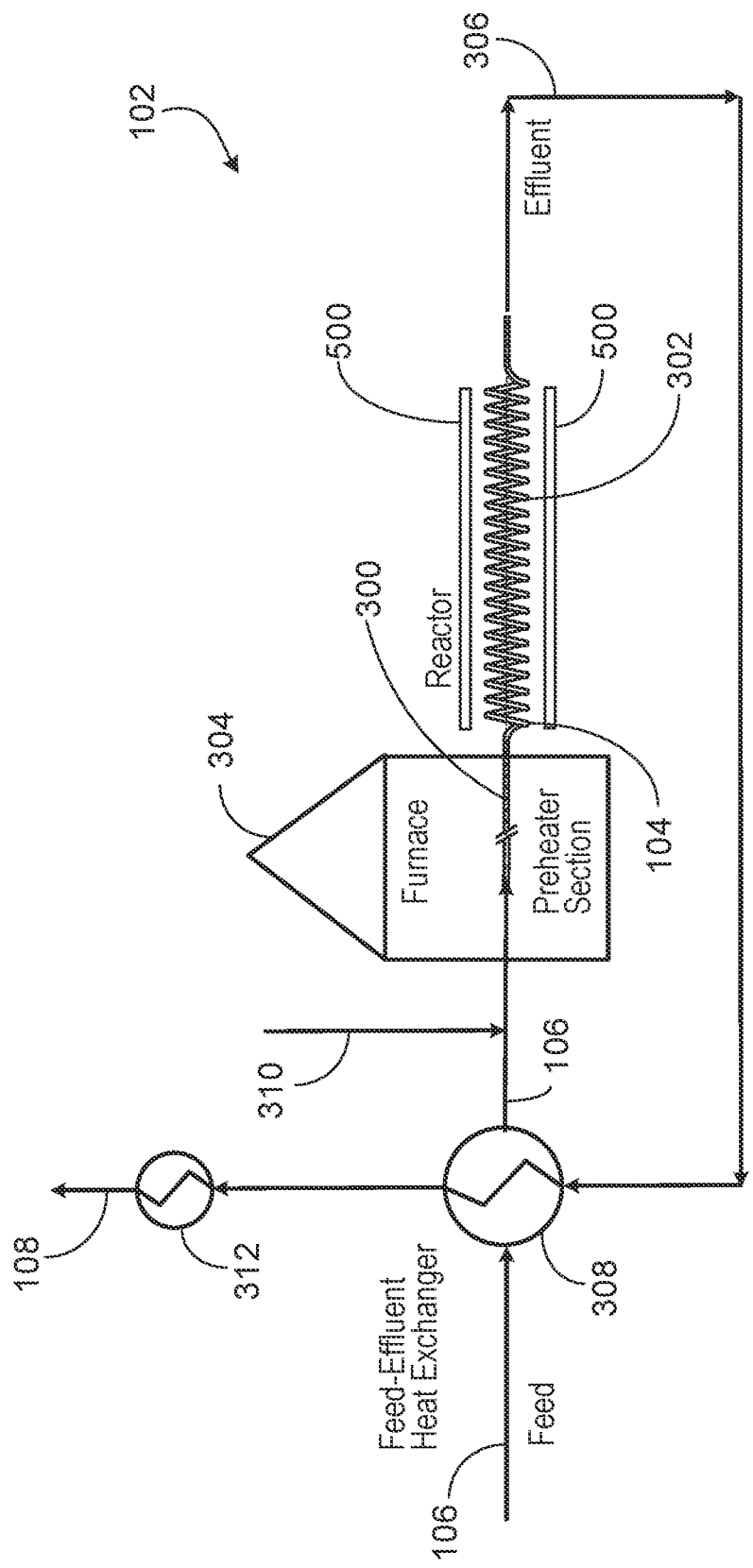
FIG. 5 is a diagram of an embodiment of the reactor system depicted in FIGS. 1-2.

FIG. 5 is an embodiment of a reactor system 102 depicted in FIGS. 1-2. In this embodiment, the reactor 104 of the reactor system 102 is a coiled tubular reactor. The reactor 104 has a straight-run section 300 at an inlet portion of the reactor 104 and a coiled tubular section 302. The reactor 104 does not include catalyst. In the illustrated embodiment, a portion of the reactor 104 is disposed in the furnace 304 (discussed above) that heats the reactor 104. In particular for the depicted implementation, the straight-run section 300 (discussed above) is situated in the furnace 304. The coiled tubular section 302 (coiled pipe) is external of the furnace 304 downstream of the furnace 304. The coiled tubular section 302 is insulated with thermal insulation, as represented by the depiction 500. The remaining depicted features of the reactor system 102 are discussed above with respect to FIGS. 1-4.

In the reactor 104 of FIGS. 1-5, the hydrodearylation cleaves the alkyl bridge, such as to break a carbon-carbon bond of the alkyl bridge (e.g., having 2 to 8 carbons). The breaking of the carbon-carbon bond may generally occur between two carbons of the alkyl bridge and occur less for the carbon-carbon bond between the alkyl bridge and one of the benzene rings. It is more likely that cracking will occur at or toward the center of the alkyl bridge chain. The rate of reaction will generally be higher for the middle carbon-carbon bond than a carbon-carbon bond adjacent to the benzene rings.

The hydrodearylation reactor may additionally perform hydrodealkylation reactions. The hydrodearylation and the hydrodealkylation may take place in parallel but generally at different reaction rates. In embodiments, the reactor 104 operating temperature may, for example, in the range of 500° C. to 700° C. and in which both hydrodearylation and hydrodealkylation occur. Operating at the low end (e.g., 500° C. to 600° C.) of that operating range may give in hydrodearylation but limited hydrodealkylation in some implementations. Hydrodealkylation may generally benefit from higher temperatures. However, at the higher temperatures, both hydrodearylation and hydrodealkylation will occur. In these thermal-treatment implementations, the operating temperature may be increased and the residence time shortened. Factors may include high temperature and short residence time, which will provides adequate energy to break the carbon-carbon bond of the alkyl bridge. Shortening the residence time will generally reduce or limit the coke formation.

As indicated, the operating temperature of the reactor 104 may be in the range of 450° C. to 775° C., 475° C. to 750° C., 500° C. to 700° C., or 550° C. to 700° C., or at least 500° C., at least 550° C., or at least 600° C. The degree of hydrodealkylation may increase at the higher temperatures within these ranges. The hydrodearylation reactions can take place at lower temperatures than hydrodealkylation temperatures. Some embodiments may have sequential reactors 104, such as a first reactor 104 (e.g., a first coiled tubular reactor) favoring hydrodearylation by operating, for example, in the operating temperature range of 500° C. to 600° C., and a second reactor 104 (e.g., a second coiled tubular reactor) increasing hydrodealkylation by operating in the temperature range greater than 600° C.

Referring to FIGS. 3 and 5, the reactor system 102 may have two reactors 104 (e.g., coiled tubular reactors) operationally disposed in series. The first reactor 104 (disposed or partially disposed in a first furnace 304) may receive the hydrocarbon feed 106. The first reactor 104 performs at least hydrodearylation on at least some of the alkyl-bridged multi-aromatic compounds present in the first reactor 104. The first reactor 104 discharges a first effluent 306 (a product effluent of the first reactor 104).

In this arrangement of two reactors 104, the first reactor 104 discharges its product effluent to the second reactor 104 that may be disposed (or partially disposed) in a second furnace 304. The product effluent from the first reactor 104 is introduced to the second reactor 104. The second reactor 104 may perform at least hydrodealkylation on aromatic compounds in the second reactor 104.

The second reactor 104 discharges a second effluent 306 (a product effluent of the second reactor 104) as a product (e.g., processed hydrocarbons 108) of the reactor system 102. This product effluent of the second reactor 104 may optionally flow through the heat exchanger 308 (feed-effluent heat exchanger) and optionally through the cooler 312 (a second heat exchanger).

For some implementations of this arrangement of two reactors 104 operationally disposed in series, the first reactor 104 may be directed to performing hydrodearylation. For instance, the operating temperature of the first reactor 104 (as provided by the first furnace 304) may be less than 600° C. or less than 650° C. For example, the operating temperature of the first reactor 104 may be in a range of 450° C. to 600° C. or in a range of 500° C. to 600° C. While some hydrodealkylation may occur at these lower operating temperatures in the first reactor 104, these temperatures are more adequate for hydrodearylation.

The second reactor 104 may be directed to performing hydrodealkylation. For instance, the operating temperature of the second reactor 104 (a provided by a second furnace 304) may be greater than 600° C. For example, the operating temperature of the second reactor 104 may be in a range of 600° C. to 750° C. or in a range of 600° C. to 700° C. Therefore, for at least this reason of a higher operating temperature, hydrodealkylation may be more prevalent in the second reactor 104 than in the first reactor 104 (at lower operating temperature). The hydrodealkylation may occur on both mono-aromatic compounds and multi-aromatic compounds.

Hydrodearylation may occur in the second reactor 104 on alkyl-bridged multi-aromatic compounds that may be received in the product effluent from the first reactor 104.

Figure 6:
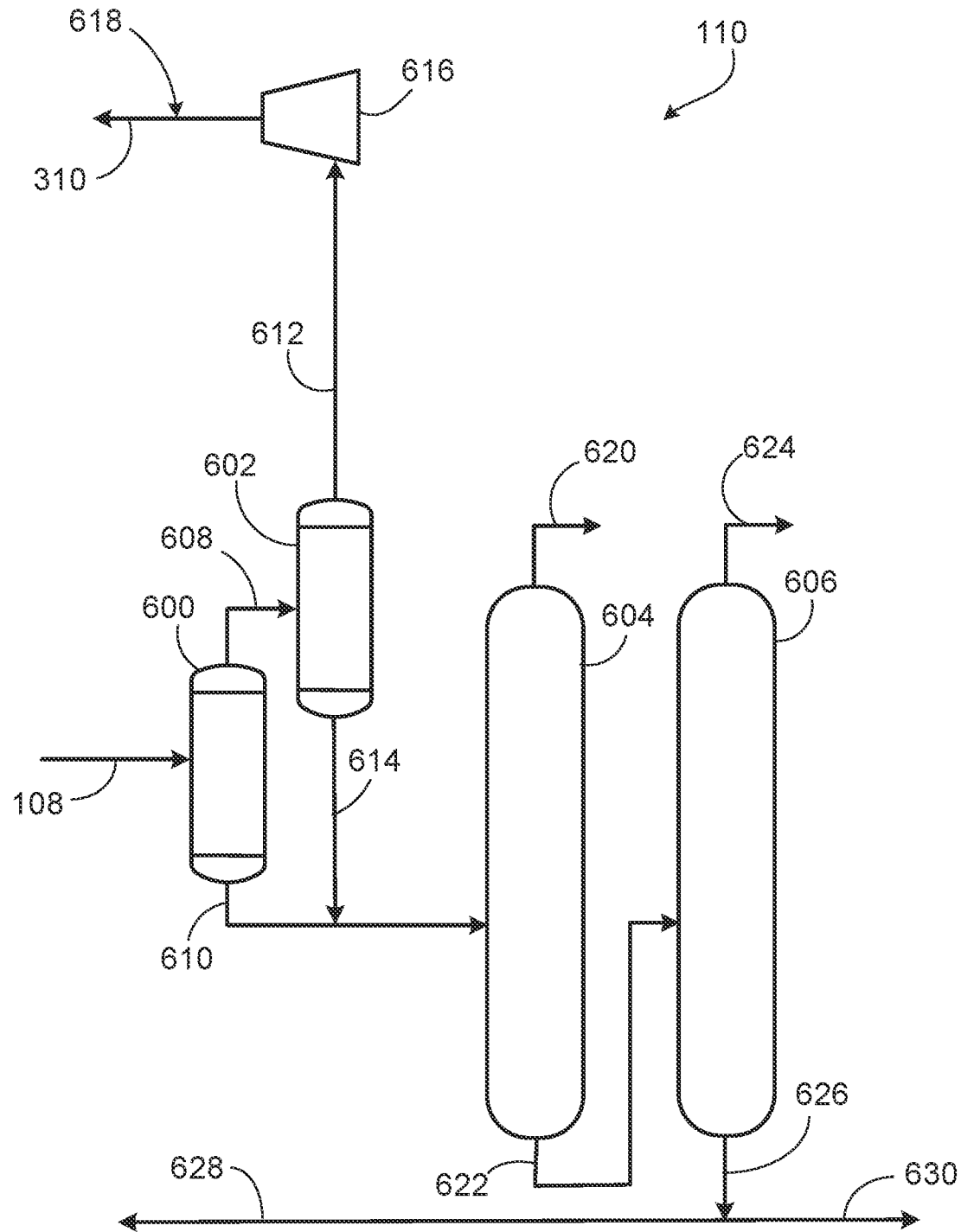
FIG. 6 is a simplified flow diagram of an embodiment of the separation system of FIGS. 1-2.

FIG. 6 is an embodiment of the separation system 110 of FIGS. 1-2. Other configurations and systems are applicable as the separation system 110. The illustrated embodiment includes a hot separator 600 (first separation vessel), a cold separator 602 (second separation vessel), a stripper column 604 (first distillation column) and a splitter column 606 (second distillation column).

The hot separator 600 and cold separator 602 may each be a vertical vessel having a volume and L/D ratio, as well as internals in some implementations, to provide for separation of gas from liquid. In implementations, operating conditions for the hot separator 600 may include a temperature in the range of 200° C. to 400° C. and a hydrogen partial pressure in the range of 5 bar gauge to 50 bar gauge. Operating conditions for the cold separator 602 may include a temperature in the range of 40° C. to 80° C. and a pressure in the range of 5 bar gauge to 50 bar gauge.

The stripper column 604 and the splitter column 606 may each be a trayed distillation column (having distillation trays) or a packed distillation column (having packing). The distillation trays may provide for distillation separation stages than can involve heat transfer and mass transfer. The packing may provide for theoretical distillation separation stages. In various embodiments, operating conditions for the stripper column 604 and the splitter column 606 may include a temperature in the range of 40° C. to 300° C. and a pressure in the range of 0.05 bar to 30 bar.

The stripper column 604 and the splitter column 606 may each be a reboiled distillation column (reboiled fractionation column) associated with a respective reboiler heat exchanger. In certain implementations, the stripper column 604 and splitter column 606 as distillation columns may have a respective overhead condenser (heat exchanger) and a reflux system. The reflux system may include an accumulator vessel to receive condensed liquid from the condenser and a pump (e.g., centrifugal pump) to pump the condensed liquid from the accumulator vessel as reflux to a side inlet on an upper portion of distillation column. In other implementations, an overhead condenser and reflux system are not employed but instead reflux may be provided to the distillation column from another source.

In operation, the processed hydrocarbons 108 stream from the hydrodearylation reactor system 102 (FIGS. 1-3 and 5) is fed via a conduit to the hot separator 600. The hot separator 600 includes an inlet to receive the processed hydrocarbons 108, an outlet to discharge an overhead gas 608, and an outlet to discharge a bottoms liquid 610. The overhead gas 608 may include, for example, hydrogen, methane, ethane, C3+ hydrocarbons, or any combinations thereof. The overhead gas 608 may exit the hot separator 600 via a conduit to a condenser heat exchanger(s) (not shown). The partially-condensed overhead gas 608 from the condenser heat exchanger may be fed via a conduit to the cold separator 602. The motive force for flow of the overhead gas 608 may be by operating pressure differential between the hot separator 600 and the cold separator 602. The cold separator 602 includes an inlet to receive the partially-condensed overhead gas 608, an outlet to discharge an overhead gas 612, and an outlet to discharge a bottoms liquid 614.

In implementations, the overhead gas 612 from the cold separator 602 may be the light components 114 discharged from the separation system 110 in FIGS. 1-2. The overhead gas 612 may be rich in hydrogen, such as greater than 60 wt % hydrogen or greater than 70 wt % hydrogen. The overhead gas 612 may be recycled via a conduit to the hydrodearylation reactor system 102. A compressor 616 (e.g., positive displacement or dynamic) may provide motive force for flow of the overhead gas 612 to the hydrodearylation reactor 104 (e.g., FIGS. 1-5) in the reactor system 102.

The compressed overhead gas stream 612 may be combined with fresh hydrogen 618 (e.g., makeup hydrogen) to give the hydrogen 310 stream (FIGS. 3 and 5) fed to the reactor 104. The make-up hydrogen 618 may be added to the compressed overhead gas stream 612 at the discharge of the separation system 110 or in the reactor system 102. The hydrogen makeup stream 618 may be a high-purity make-up gas containing substantially hydrogen from a header. In some implementations, the combined stream (hydrogen 310) may be recycled back to the reactor 104 through the header.

The bottoms liquid 614 stream from the cold separator 602 may be preheated in a heat exchanger train (not shown). The heated bottoms liquid 614 stream may be combined with the bottoms liquid 610 stream from the hot separator 600, and the combined stream fed through a conduit to the stripper column 604.

The stripper column 604 may form two streams including an overhead vapor 620 and a bottoms liquid 622. The overhead vapor 620 may be condensed and a portion of the condensed liquid conveyed as liquid reflux for the stripper column 604. The remaining partially-condensed overhead vapor 620 may be routed for further processing. By way of example, the partially-condensed overhead vapor 620 may be processed in an aromatics complex (e.g., 202 of FIG. 2) in a reformate splitter column or a within a para-xylene aromatics unit. The stream 620 may be analogous to a first product stream 118 of FIGS. 1-2.

The bottoms liquid 622 from stripper column 604 may be routed into the splitter column 606. The splitter column 606 may form two streams including an overhead vapor 624 and a heavy bottoms liquid 626. The overhead vapor 624 may be include C6+ compounds. The bottoms liquid 626 may include C10+ compounds. The overhead vapor 624 may be condensed and portion of the condensed liquid sent as liquid reflux to the splitter column 606. A portion of the condensed overhead vapor 624 that is not refluxed to the splitter column 606 may be routed for further processing. By way of example, this portion may be routed to an aromatics complex a reforming/para-xylene unit an aromatics complex (e.g., 202 of FIG. 2) for xylene recovery. The heavy bottoms liquid 626 (e.g., analogous to heavy components 116 stream of FIGS. 1-2) may be split, for example, into two streams including a recycle stream 628 (to the reactor 104) and a bleed stream 630. A flow rate of the bleed stream 630 may be adjusted to promote that heavy aromatic hydrocarbons do not buildup in the reactor system 102 or separation system 110. The recycle stream 628 may analogous to the recycle 116A of FIGS. 1-2. The bleed stream 630 may be analogous to the portion 116B of FIGS. 1-2.

Figure 7:
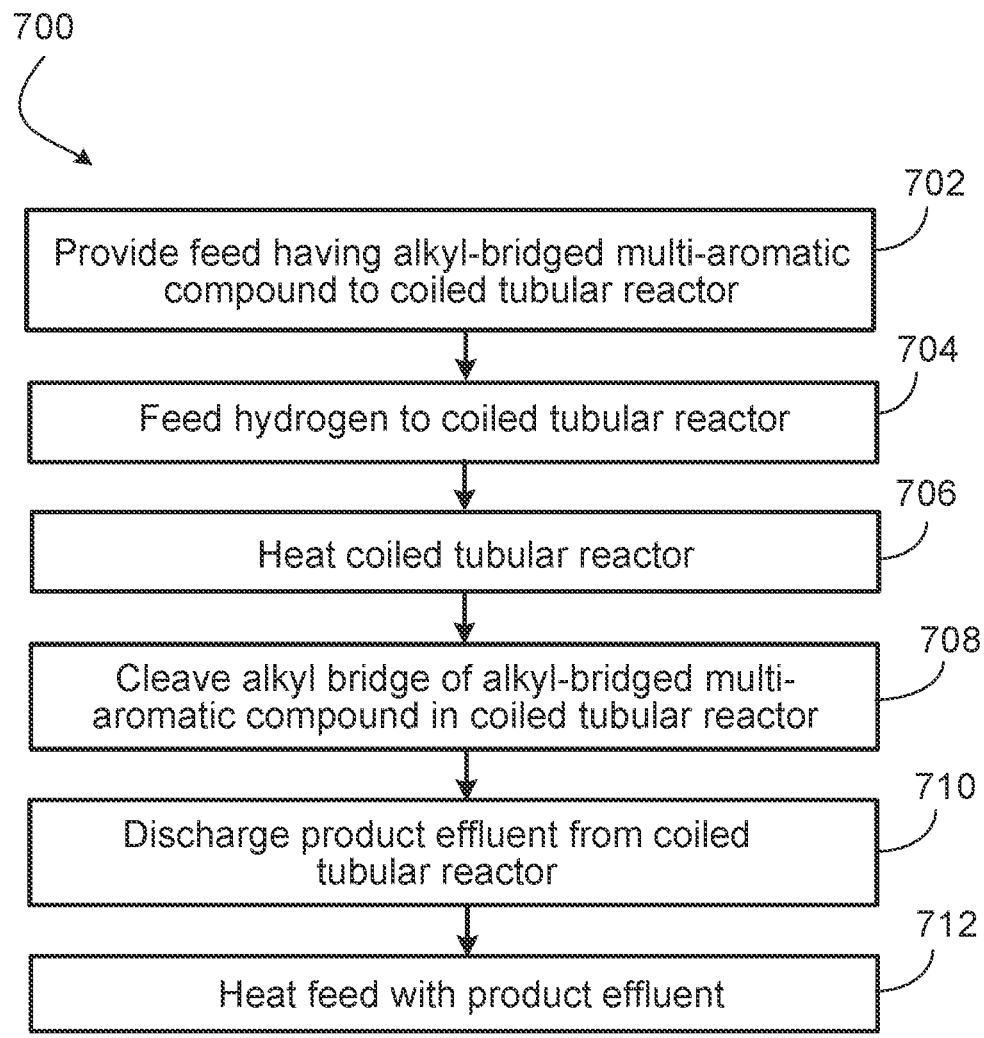
FIG. 7 is a block flow diagram of a method of processing alkyl-bridged multi-aromatic compounds.

FIG. 7 is a method 700 of processing alkyl-bridged multi-aromatic compounds. At block 702, the method includes providing a feed having alkyl-bridged multi-aromatic compounds to a coiled tubular reactor. The alkyl-bridged multi-aromatic compounds may include non-condensed alkyl-bridged multi-aromatic compounds. An example of an alkyl-bridged multi-aromatic compound is a compound having a first aromatic ring coupled via an alkyl bridge to a second aromatic ring, wherein the alkyl bridge has at least two carbons (e.g., 2 to 8 carbons). Examples of a source of the feed is a C9+ reject stream from an aromatics complex or a C11+ reject stream from an aromatics complex.

At block 704, the method includes feeding hydrogen to the coiled tubular reactor. The hydrogen may be added to the feed or directly to the reactor, or both. As discussed above for certain embodiments, the hydrogen may include both fresh hydrogen (makeup) and recycle hydrogen.

At block 706, the method includes heating the coiled tubular reactor. For example, at least a portion of the coiled tubular reactor may be situated in a furnace for the heating of the reactor. In some implementations, the coiled tubular reactor may have an inlet portion (e.g., straight-run pipe) as a preheater section in the furnace.

At block 708, the method includes cleaving the alkyl bridge of alky-bridged multi-aromatic compounds in the coiled-tubular reactor. The cleaving of the alkyl bridge includes breaking a bond between two carbons of the at least two carbons of the alkyl bridge. This cleaving is performed in the presence of hydrogen and may be labeled as hydrodearylation. The percent of the alky-bridged multi-aromatic compounds in the reactor that experience hydrodearylation may be in the range of 5% to 100%, depending on operating conditions in the reactor and other factors.

In an example, in the coiled tubular reactor, the cleaving of an alkyl bridge may separate an alkyl-bridged multi-aromatic compound into a first aromatic compound having the first aromatic ring and a second aromatic compound having the second aromatic ring. One or more additional aromatic rings may be present in the first aromatic compound and the second aromatic compound. Lastly, hydrodealkylation may also be performed in the coiled tubular reactor in parallel with the hydrodearylation.

At block 710, the method includes discharging a product effluent from the coiled tubular reactor. The product effluent may generally include a greater amount of lighter aromatics than in the feed introduced to the coiled tubular reactor. The product effluent may typically also include unreacted hydrogen. In other words, a certain amount of the hydrogen added (block 704) may not react in the coiled tubular reactor and is discharged in the product effluent.

At block 712, the method may optionally include heating the feed with the product effluent, such as in a heat exchanger. Heat transfer occurs from the product effluent to the feed. The heat exchanger may be, for example, a shell-and-tube heat exchanger. In some implementations in the heat exchanger, the flow of the effluent may be countercurrent with the flow of the feed.

EXAMPLES

Figure 8:
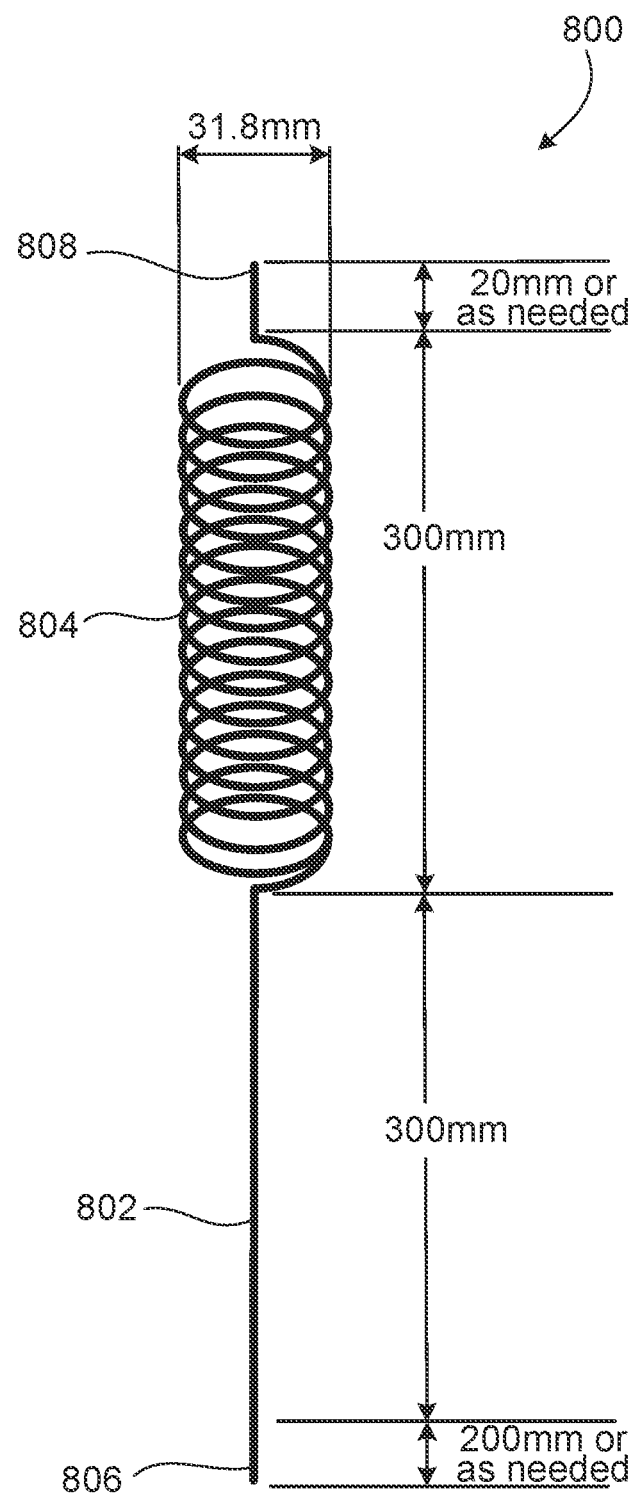
FIG. 8 is a perspective of a coiled tubular reactor that is a representation of the three coiled tubular reactors in the pilot plant utilized to perform the Examples.

FIG. 8 is a coiled tubular reactor 800 that is a representation of the three coiled tubular reactors A, B, and C (in the pilot plant) utilized to perform the Examples. The coiled tubular reactor 800 is ⅛ inch stainless-steel tubing having a straight tubing section 802 (upstream portion) and a coiled tubing section 804 (downstream portion). The straight tubing section 802 is 300 mm in length. Likewise, the coiled tubing section 804 is 300 mm in longitudinal length. The coiled tubing section 804 has a spiral outer diameter (OD) of 31.8 mm. The reactor 800 includes an inlet portion 806 of about 200 mm that may be adjusted and an outlet portion 808 of about 20 mm that may be adjusted.

Figure 9:
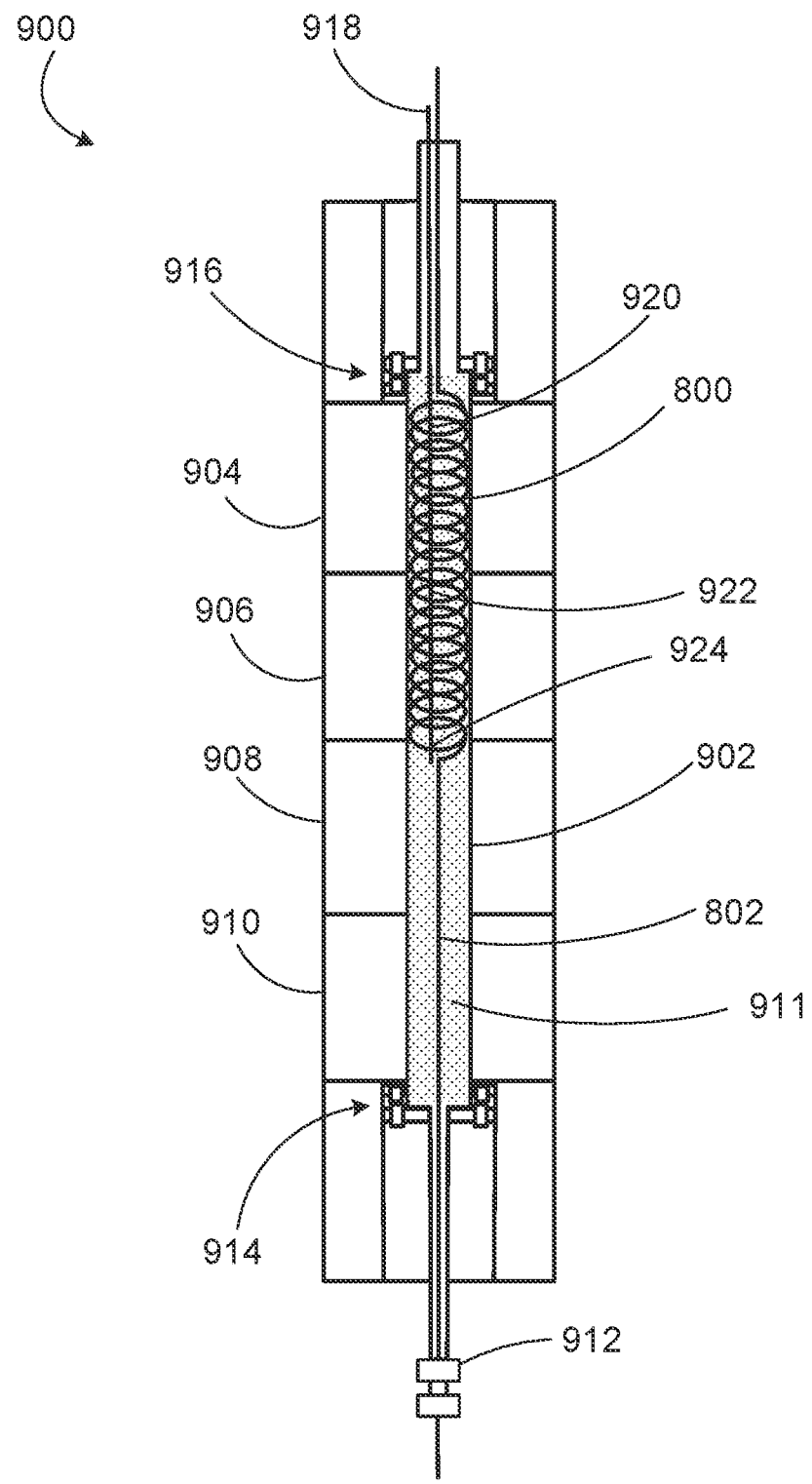
FIG. 9 is a diagram of a coiled-tubular reactor unit that is a representation of the three coiled-tubular reactor units utilized to perform the Examples.

FIG. 9 is a coiled-tubular reactor unit 900 that is a representation of the three coiled-tubular reactor units having the three respective coiled tubular reactors 800 utilized to perform the Examples. The reactor unit 900 includes an outer casing 902 around the reactor 800. Surrounding the casing 902 are four heating sections 904, 906, 908, and 910. The heating sections 904, 906, 908, and 910 are sections of straight-walled heater in which the reactor 800 can be inserted. The heating sections 904, 906, 908, and 910 can be independently controlled. The reactor unit 900 includes 70-mesh silicon carbide 911 in the casing 902 to promote heat transfer from the heating sections 904, 906, 908, and 910 to the reactor 800.

The inlet portion of the reactor unit 900 includes a bored-through reducer union 912 and bottom flanges 914. The outlet portion of the reactor unit 900 includes top flanges 916. Further, the reactor unit 900 includes thermowells 918 having respective thermocouples for measuring temperature at three longitudinal positions 920, 922, and 924 along the coiled tubing section 804 (see FIG. 8). The thermowells 918 are inserted into the outer casing 902 adjacent the coiled tubing section 804 of the reactor 800.

Table 1 below gives various dimensions of each of the pilot-plant reactors A, B, and C utilized to perform the three respective tests as Examples. The operating conditions for the three respective tests are also given in Table 1. The values for pressure, temperature, and feed rate are measured values. Calculated values for residence time are in the range of 2 seconds to 557 seconds. Lastly, analysis of the product effluent discharged from the pilot-plant reactors A, B, and C in the three respective tests showed an 8% drop in the number of di-aromatic compounds in the product effluent as compared to the feed. The analysis was by comprehensive two-dimensional gas chromatography (GC×GC) also known as 2D-GC.

TABLE 1

| Pilot Plant Reactor Data and Operating Conditions | | | | |
|---|---|---|---|---|
| | Units | Reactor A | Reactor B | Reactor C |
| Tubing OD | mm | 3.175 | 3.175 | 3.175 |
| Tubing Thickness | mm | 0.500 | 0.880 | 1.240 |
| Tubing ID | mm | 2.175 | 1.415 | 0.695 |
| Tubing Surface Area | mm2 | 3.714 | 1.572 | 0.379 |
| Number of Spirals | | 21 | 16 | 16 |
| Pitch | mm | 16 | 16 | 16 |
| Circumference (Spiral OD) | mm | 99.85 | 99.85 | 99.85 |
| Length of Spiral | mm | 2123.6 | 1618.0 | 1618.0 |
| Volume of Spiral | cm3 | 7.886 | 2.543 | 0.614 |
| Pressure | bar | 41 | 41 | 41 |
| Temperature | ° C. | 550 | 550 | 550 |
| Feed Rate (min) | mL/hr | 51 | 51 | 51 |
| Feed Rate (max) | mL/hr | 984 | 984 | 984 |
| Residence Time (max) | sec | 556.7 | 179.5 | 43.3 |
| Residence Time (min) | sec | 28.9 | 9.3 | 2.2 |

An embodiment is a method of processing alkyl-bridged multi-aromatic compounds. The method includes providing a feed including an alkyl-bridged multi-aromatic compound to a coiled tubular reactor (e.g., having an operating temperature of at least 550° C.). The alkyl-bridged multi-aromatic compound includes a first aromatic ring coupled via an alkyl bridge (having at least two carbons) to a second aromatic ring. The feed may also have hydrogen. The method may include flowing a reaction mixture having the feed and hydrogen through the coiled tubular reactor. In certain implementations, residence time of the reaction mixture in the coiled tubular reactor may be less than 60 seconds. The method includes heating (e.g., via a furnace) the coiled tubular reactor and cleaving the alkyl bridge (e.g., breaking a bond between two carbons of the at least two carbons in presence of hydrogen but in absence of catalyst) in the coiled tubular reactor. Such separates the alkyl-bridged multi-aromatic compound into a first aromatic compound having the first aromatic ring and a second aromatic compound having the second aromatic ring. The cleaving of the alkyl bridge may be via hydrodearylation (e.g., involving thermal cracking in presence of hydrogen). The method may include performing hydrodealkylation on mono-aromatic compounds in the coiled tubular reactor in presence of hydrogen, wherein the mono-aromatic compounds may include the first aromatic compound or the second aromatic compound, or both, and wherein the mono-aromatics may include mono-aromatic compounds from the feed. The method may include preheating the feed in a heat exchanger upstream of the coiled tubular reactor or in an inlet portion of the coiled tubular reactor, or both, wherein the coiled tubular reactor includes coiled piping, and wherein the inlet portion is straight piping upstream of the coiled piping. The method may include discharging an effluent from the coiled tubular reactor to a separation system having a separation vessel, wherein average molecular weight of compounds in the effluent is less than average molecular weight of compounds in the feed, and wherein preheating includes heating the feed in the heat exchanger with the effluent.

Another embodiment is a method of processing alkyl-bridged multi-aromatic compounds. The method includes feeding alkyl-bridged multi-aromatic compounds each having an alkyl bridge to a coiled tubular reactor, wherein the coiled tubular reactor does not include catalyst. The method includes feeding hydrogen to the coiled tubular reactor and providing heat from a furnace to heat the coiled tubular reactor, wherein at least a portion of the coiled tubular reactor is disposed in the furnace. The method includes performing hydrodearylation on the alkyl-bridged multi-aromatic compounds in the coiled tubular reactor via the hydrogen and via the heat provided by the furnace. The hydrodearylation involves breaking a carbon-carbon bond of the alkyl bridge of at least some of the alkyl-bridged multi-aromatic compounds. The method may include (1) performing hydrodealkylation on aromatic compounds in the coiled tubular reactor, (2) operating the coiled tubular reactor as a continuous reactor, wherein residence time through the coiled tubular reactor is less than 100 seconds, and (3) discharging a product effluent from the coiled tubular reactor.

Yet another embodiment is a method of operating a hydrodearylation reactor. The method includes preheating a hydrocarbon feed having alkyl-bridged multi-aromatic compounds. The method includes flowing the hydrocarbon feed and hydrogen through a coiled tubular reactor and heating the coiled tubular reactor with a furnace, wherein at least a portion of the coiled tubular reactor is disposed in the furnace. In some implementations, the residence time through the coiled tubular reactor is less than 50 seconds. In certain implementations, the heating of the coiled tubular reactor with the furnace may include heating the contents of the coiled tubular reactor to at least 550° C. In particular implementations, the heating of the coiled tubular reactor with the furnace may provide the preheating of the hydrocarbon feed in a straight-run section of the coiled tubular reactor disposed in the furnace. The method includes breaking a carbon-carbon bond of an alkyl bridge in the coiled tubular reactor in absence of catalyst. The method includes discharging an effluent from the coiled tubular reactor. The preheating of the hydrocarbon feed may involve heating the hydrocarbon feed with the effluent. The method may include performing hydrodealkylation in the coiled tubular reactor. The method may include injecting steam into the hydrocarbon feed or directly into the coiled tubular reactor, or both, to reduce coke formation in the coiled tubular reactor or reduce plugging of the coiled tubular reactor. The method may include adding at least one of alkyl sulfide or disulfides to the hydrocarbon feed or directly to the coiled tubular reactor, or both, to reduce coke formation in the coiled tubular reactor and to protect an interior metal surface of the coiled tubular reactor.

Yet embodiment is a method of processing alkyl-bridged multi-aromatic compounds, involving providing a feed having aromatic compounds including an alkyl-bridged multi-aromatic compound to a first coiled tubular reactor. The alkyl-bridged multi-aromatic compound has a first aromatic ring coupled via an alkyl bridge (at least two carbons) to a second aromatic ring. The method includes heating (e.g., via a first furnace) the contents of the first coiled tubular reactor to a temperature of in a range of 450° C. to 600° C. or in a range of 500° C. to 600° C. This may be characterized as an operating temperature of the first coiled tubular reactor. The method includes cleaving the alkyl bridge in the first coiled tubular reactor to separate the alkyl-bridged multi-aromatic compound into a first aromatic compound having (or that is) the first aromatic ring and a second aromatic compound having (or that is) the second aromatic ring. This cleaving of the alkyl bridge is hydrodearylation. The method includes discharging a product effluent (processed feed) from the first coiled tubular reactor to a second coiled tubular reactor. This product effluent from the first coiled tubular reactor is introduced into the second coiled tubular reactor. The contents of the second coiled tubular reactor are heated (e.g., via a second furnace) to at least (or greater than) 600° C., such as in a range of 600° C. to 750° C. or in a range of 600° C. to 700° C. This may be characterized as an operating temperature of the second coiled tubular reactor. The method includes performing hydrodealkylation on aromatic compounds in the second coiled tubular reactor. The aromatic compounds may include aromatic compounds received in the product effluent from the first reactor. The hydrodealkylation may occur on both mono-aromatic compounds and multi-aromatic compounds. The hydrodealkylation may occur on the aforementioned first aromatic compound and second aromatic compound. Hydrodearylation may occur in the second reactor on alkyl-bridged multi-aromatic compounds, such as those that may be received in the product effluent from the first reactor.

Yet another embodiment is a hydrocarbon processing system having a hydrodearylation reactor system that receives hydrocarbon feed and hydrogen. The hydrocarbon feed includes an alkyl-bridged multi-aromatic compound having a first aromatic ring coupled via an alkyl bridge to a second aromatic ring. The hydrodearylation reactor system may include a conduit operationally coupled to an aromatics complex to receive at least a portion of the hydrocarbon feed having alkyl-bridged multi-aromatic compounds from the aromatics complex. The hydrodearylation reactor system includes a hydrodearylation reactor that is a coiled tubular reactor to break a carbon-carbon bond of the alkyl bridge in presence of hydrogen to separate the first aromatic ring from the second aromatic ring, wherein the coiled tubular reactor does not include catalyst. The hydrodearylation reactor system includes a furnace (e.g., a direct fired heater) to heat the coiled tubular reactor, wherein at least a portion of the coiled tubular reactor is disposed in the furnace.

The hydrocarbon processing system further includes a separation system that receives an effluent including unreacted hydrogen from the coiled tubular reactor. The separation system has a cold separator vessel that discharges overhead light components including unreacted hydrogen and also discharges bottoms liquid. The hydrocarbon processing system may have a compressor to increase pressure of the lights components and a conduit to convey the light components from the compressor to the hydrodearylation reactor system for recycle of unreacted hydrogen to the hydrodearylation reactor. The separation system may have a hot separator vessel to receive the effluent from the coiled tubular reactor, discharge an overhead gas including unreacted hydrogen from the effluent to the cold separator vessel, and discharge bottoms liquid. The hydrocarbon processing system may include a heat exchanger disposed operationally upstream of the hot separator to heat the hydrocarbon feed with the effluent. The hydrocarbon processing system may include a second heat exchanger to cool the effluent discharged from the heat exchanger. The separation system may include a stripper column that receives the bottoms liquid from the hot separator vessel and the bottoms liquid from the cold separator vessel. If employed, the stripper column discharges an overhead vapor to an aromatics complex and discharges bottoms liquid to a splitter column. The separation system may include a splitter column that discharges an overhead vapor having C6+ compounds including mixed xylenes and that discharges bottoms liquid having C10+ compounds. A conduit may convey at least a portion of the bottoms liquid from the splitter column to the hydrodearylation reactor system.

Yet another embodiment is an aromatics processing system including an aromatics complex having a xylene distillation column that discharges an overhead stream including mixed xylenes and discharges a bottoms stream including C9+ aromatic compounds. The aromatics processing system includes a coiled tubular reactor (e.g., not having catalyst) that receives feed having at least a portion of the bottoms stream including alkyl-bridged multi-aromatic compounds. The coiled tubular reactor breaks a carbon-carbon bond of an alkyl bridge of an alkyl-bridged multi-aromatic compound and discharges a product effluent. The aromatics processing system includes (1) a conduit to add hydrogen to the feed upstream of the coiled tubular reactor or directly to the coiled tubular reactor, (2) a furnace that provides heat to the coiled tubular reactor (wherein at least a portion of the coiled tubular reactor is disposed in the furnace), and (3) a heat exchanger that heats the feed with the product effluent. The aromatics processing system may include a separation system having a separation vessel. The separation system receives the product effluent and discharges unreacted hydrogen and C10+ compounds to the coiled tubular reactor.

Yet another embodiment is a hydrodearylation reactor system including a feed conduit operationally coupled to an aromatics complex to receive a hydrocarbon feed including alkyl-bridged multi-aromatic compounds. The aromatics complex includes a distillation column. The hydrodearylation reactor system has a coiled tubular reactor operationally coupled to the feed conduit that receives the hydrocarbon feed and cleaves an alkyl bridge of an alkyl-bridge multi-aromatic compound of the received alkyl-bridge multi-aromatic compounds in presence of hydrogen. In implementations, the coiled tubular reactor does not have catalyst. The hydrodearylation reactor system includes a hydrogen conduit to add hydrogen to the feed conduit or directly to the coiled tubular reactor. The hydrogen conduit can include a first hydrogen conduit to add hydrogen to the feed conduit and a second hydrogen conduit to add hydrogen directly to the coiled tubular reactor. The reactor system includes a (1) furnace (e.g., direct fired heater) that heats the coiled tubular reactor, (2) a discharge conduit to discharge an effluent from the coiled tubular reactor, and (3) a heat exchanger that heats the hydrocarbon feed with the effluent. The coiled tubular reactor may discharge the effluent via the discharge conduit through the heat exchanger to a separation system (having a separation vessel). A second heat exchanger may cool the effluent discharged from the heat exchanger. The feed conduit may be operationally coupled to the separation system to receive C10+ components from the separation system. The reactor system may receive at least some of the hydrogen via the hydrogen conduit from the separation system.

The coiled tubular reactor may have a straight-run piping section and a coiled piping section. If so, the straight-run piping section may be an inlet portion upstream of the coiled piping section. The coiled piping section may be spirals of piping coiled around a longitudinal axis of the coiled tubular reactor. In some implementations, the straight-run piping section is a preheater section of the coiled tubular reactor. In certain implementations, the length of the straight-run piping section is greater than a longitudinal length of the coiled piping section.

Yet another embodiment is a hydrodearylation reactor system including a feed conduit operationally coupled to an aromatics complex to receive hydrocarbon feed having aromatic compounds including alkyl-bridged multi-aromatic compounds from the aromatics complex. The aromatics complex includes at least one distillation column. The hydrodearylation reactor system includes a first coiled tubular reactor operationally coupled to the feed conduit to receive the aromatic compounds and to cleave an alkyl bridge of an alkyl-bridged multi-aromatic compound in presence of hydrogen. The hydrodearylation reactor system includes: a first hydrogen conduit to add hydrogen to the feed conduit or directly to the first coiled tubular reactor; a first furnace to heat contents of the first coiled tubular reactor to a temperature in a range of 450° C. to 600° C.; and a first discharge conduit to discharge a first effluent from the first coiled tubular reactor to a second coiled tubular reactor. The hydrodearylation reactor system includes the second coiled tubular reactor to perform hydrodealkylation on aromatic compounds in the second coiled tubular reactor, and a second furnace to heat contents of the second coiled tubular reactor to a temperature of greater than 600° C. In implementations, the hydrodearylation reactor system may also include: a second hydrogen conduit to add hydrogen to the first discharge conduit or directly to the second coiled tubular reactor; a second discharge conduit to discharge a second effluent from the second coiled tubular reactor; and a shell-and-tube heat exchanger to heat the hydrocarbon feed with the second effluent. In implementations, the first coiled tubular reactor and the second coiled tubular reactor each do not have catalyst. The first coiled tubular reactor and the second tubular reactor may each have a straight-run piping section and a coiled piping section. The straight-run piping section may be an inlet portion (of the coiled tubular reactor) upstream of the coiled piping section.

A number of implementations have been described. Nevertheless, it will be understood that various modifications may be made without departing from the spirit and scope of the disclosure.

What is claimed is:

1. A hydrodearylation reactor system comprising:
    a feed conduit operationally coupled to an aromatics complex to receive a hydrocarbon feed comprising alkyl-bridged multi-aromatic compounds, the aromatics complex comprising a distillation column;
    a coiled tubular reactor operationally coupled to the feed conduit to receive the hydrocarbon feed and to cleave an alkyl bridge of an alkyl-bridged multi-aromatic compound of the alkyl-bridge multi-aromatic compounds in presence of hydrogen;
    a hydrogen conduit to add hydrogen to the feed conduit or directly to the coiled tubular reactor;
    a furnace to heat the coiled tubular reactor;
    a discharge conduit to discharge an effluent from the coiled tubular reactor; and
    a heat exchanger to heat the hydrocarbon feed with the effluent.

2. The system of claim 1, wherein the coiled tubular reactor does not comprise catalyst, wherein the coiled tubular reactor comprises a straight-run piping section and a coiled piping section, the straight-run piping section comprising an inlet portion upstream of the coiled piping section, wherein the coiled piping section comprises spirals of piping coiled around a longitudinal axis of the coiled tubular reactor, and wherein the furnace comprises a direct fired heater.

3. The system of claim 2, wherein the straight-run piping section comprises a preheater section of the coiled tubular reactor, and wherein a length of the straight-run piping section is greater than a longitudinal length of the coiled piping section.

4. The system of claim 1, wherein the coiled tubular reactor to discharge the effluent via the discharge conduit through the heat exchanger to a separation system and to receive hydrogen via the hydrogen conduit from the separation system, the separation system comprising a separation vessel.

5. The system of 37, wherein the feed conduit is operationally coupled to the separation system to receive C10+ components from the separation system.

6. The system of claim 1, comprising a second heat exchanger to cool the effluent discharged from the heat exchanger.

7. The system of claim 1, wherein the hydrogen conduit comprises a first hydrogen conduit to add hydrogen to the feed conduit and a second hydrogen conduit to add hydrogen directly to the coiled tubular reactor.

8. A hydrodearylation reactor system comprising:
a feed conduit operationally coupled to an aromatics complex to receive hydrocarbon feed comprising aromatic compounds comprising alkyl-bridged multi-aromatic compounds from the aromatics complex, the aromatics complex comprising a distillation column;
a first coiled tubular reactor operationally coupled to the feed conduit to receive the aromatic compounds and to cleave an alkyl bridge of an alkyl-bridged multi-aromatic compound in presence of hydrogen;
a first hydrogen conduit to add hydrogen to the feed conduit or directly to the first coiled tubular reactor;
a first furnace to heat contents of the first coiled tubular reactor to a temperature in a range of 450° C. to 600° C.;
a first discharge conduit to discharge a first effluent from the first coiled tubular reactor to a second coiled tubular reactor;
the second coiled tubular reactor to perform hydrodealkylation on aromatic compounds in the second coiled tubular reactor; and
a second furnace to heat contents of the second coiled tubular reactor to a temperature of greater than 600° C.

9. The system of claim 8, comprising a second hydrogen conduit to add hydrogen to the first discharge conduit or directly to the second coiled tubular reactor.

10. The system of claim 8, comprising:
comprising a second discharge conduit to discharge a second effluent from the second coiled tubular reactor; and
a shell-and-tube heat exchanger to heat the hydrocarbon feed with the second effluent.

11. The system of claim 8, wherein the first coiled tubular reactor and the second coiled tubular reactor each do not comprise catalyst, wherein the first coiled tubular reactor and the second tubular reactor each comprise a straight-run piping section and a coiled piping section, the straight-run piping section comprising an inlet portion upstream of the coiled piping section.

* * * * *